United States Patent [19]

Chin et al.

[11] Patent Number: 5,166,455
[45] Date of Patent: Nov. 24, 1992

[54] PROCESS FOR THE PRODUCTION OF TERTIARY ALKYTL ETHERS FROM FCC LIGHT NAPHTHA

[75] Inventors: Arthur A. Chin; Frederick J. Krambeck, both of Cherry Hill, N.J.; Stephen S. Wong, Singapore, Sweden; Sergei Yurchak, Media, Pa.

[73] Assignee: Mobil Oil Corporation, Fairfax, Va.

[21] Appl. No.: 821,374

[22] Filed: Jan. 16, 1992

[51] Int. Cl.$^5$ .............................. C07C 41/06
[52] U.S. Cl. ...................... 568/697; 585/314; 585/315
[58] Field of Search ......................... 568/697

[56] References Cited

U.S. PATENT DOCUMENTS 4,554,386 11/1985 Groenveld .
4,788,365 11/1988 Harandi .
4,826,507 5/1989 Harandi .
4,886,925 12/1989 Harandi .

*Primary Examiner*—Howard T. Mars
*Attorney, Agent, or Firm*—Alexander J. McKillop; Charles J. Speciale; L. G. Wise

[57] ABSTRACT

A process has been discovered for the conversion of $C_5$–$C_7$ olefinic hydrocarbons, such as those contained in FCC light naphtha, to iso-butene-rich and isoamylene-rich streams in an integrated process for the production of MTBE and TAME. The process involves the initial separation of the isoamylene-rich $C_5$-fraction of the feedstream which is converted to TAME. The $C_6$–$C_7$ fraction plus unreacted $C_5$'s are converted by olefin interconversion with medium pore zeolite catalyst into an isobutylene and isoamylene-rich stream which is then used as feedstream for etherification to MTBE and TAME.

20 Claims, 1 Drawing Sheet

PROCESS FOR THE PRODUCTION OF TERTIARY ALKYTL ETHERS FROM FCC LIGHT NAPHTHA

This invention relates to a process for the production of alkyl tertiary alkyl ethers from $C_5$-$C_7$ olefins. The invention particularly relates to an integrated process for the production of tertiary alkyl ethers by interconversion of light olefins in FCC light naphtha and the conversion of isoolefins to methyl tertiary butyl ether (MTBE) and methyl tertiary amyl ether (TAME).

BACKGROUND OF THE INVENTION

It is known that isobutylene and other isoalkenes, or iso-olefins, produced by hydrocarbon cracking may be reacted with methanol and other $C_1$-$C_4$ lower aliphatic alcohols, or alkanol, over an acidic catalyst to provide methyl tertiary butyl ether (MTBE) or the like. Generally, it is known that asymmetrical ethers having the formula $(CH_3)3C-O-R$, where R is a $C_1$-$C_4$ alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+0=83) octane, the blending value of MTBE at the 10% level is about 103. On the other hand, for an (R+0) of 95 octane fuel, the blending value of 10% MTBE is about 114.

The liquid phase reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable. Typically, with acid resin catalyst the etherification reaction is carried out in liquid phase. However, mixed phase etherification is known, particularly where the catalyst is contained as a fixed bed in a fractionator which serves to both separate the reaction products and operate as a vessel to contain the catalyst under etherification conditions.

Typical hydrocarbon feedstock materials for etherification reactions include olefinic streams, such as cracking process light gas containing butene isomers in mixture with substantial amounts of paraffins including n-butane and isobutane The $C_4$ components usually contain a major amount of unsaturated compounds, such as 10-40% isobutylene, 20-55% linear butenes, and small amounts of butadiene. Also, $C_4$+heavier olefinic hydrocarbon streams may be used, particularly mixtures of isobutylene and isoamylene and $C_5$+ streams containing isoamylene. To augment the sources of feedstock for $C_4$-$C_5$ isoolefins for conversion to MTBE and TAME it is desirable to employ light olefins-rich fractions from olefinic gasoline, typically the light naphtha fraction from fluid catalytic cracking (FCC) processes.

In M. N. Harandi U.S. Pat. No. 4,886,925, incorporated herein by reference, an integrated process is disclosed for the conversion of $C_2$+ normal olefins into higher isoolefins with etherification to provide methyl tertiary alkyl ethers and high octane gasoline. The process combines olefins interconversion with etherification and conversion of unreacted methanol and olefins in contact with acidic, shape selective metallosilicate zeolite catalyst.

In the process for catalytic conversion of oxygenate and/or olefins to heavier hydrocarbons by catalytic oligomerization using an acid crystalline zeolite, such as ZSM-5 type catalyst, process conditions can be varied to favor the formation of either gasoline, distillate, lube range products or aromatics. Light olefins can be oligomerized to high molecular weight distillate range olefins over ZSM-5. Olefin molecular weight growth through a sequence of oligomerization and cracking reactions is thermodynamically forced at relatively high pressures of about 5600 kPa (800 psia) and relatively low temperatures of about 260° C. (500° F.). At much lower pressure and higher temperature, thermodynamics restrict the olefin distribution to low molecular weight. This is the basis for the olefin interconversion process, i.e., to operate under conditions where lower olefins can be converted to an equilibrium distribution of olefins with iso-butenes and iso-pentenes maximized. The olefin interconversion process can use fixed bed, moving bed or fluid bed reactors containing zeolite type catalysts such as ZSM-5. Operating conditions encompass temperatures between 200 and 400° C. and low pressures, generally between 100 and 1500 kPa. The olefin interconversion process provides a unique method to optimize the concentration of isoolefins in a mixture of light olefins.

Accordingly, it is an object of the present invention to provide a process for the production of high octane value alkyl tertiary alkyl ethers.

Another object of the invention is to provide high octane value ethers using a light gasoline fraction such as FCC light naphtha as feedstock by conversion to isoolefin-rich feedstock.

Another object of the invention is to provide a process for the production of isoolefins for MTBE and TAME production by olefin interconversion of $C_5$-$C_7$ olefinic hydrocarbons.

SUMMARY OF THE INVENTION

A process has been discovered for the conversion of $C_5$-$C_7$ olefinic hydrocarbons, such as those contained in FCC light naphtha, to isobutylene-rich and isoamylene-rich streams in an integrated process for the production of MTBE and TAME. The process involves the initial separation of the isoamylene-rich $C_5$-fraction of the feedstream which is converted to TAME. The $C_6$-$C_7$ fraction plus unreacted $C_5$'s are converted by olefin interconversion with medium pore zeolite catalyst into an isobutylene and isoamylene-rich stream which is then used as feedstream for etherification to MTBE and TAME. The process advantageously expands the range of petroleum fractions useful in the production of MTBE and TAME while lowering the olefinic content of light gasoline fractions.

More particularly, a process for the production of high octane value alkyl tertiary alkyl ethers is disclosed wherein a feedstream comprising $C_5$-$C_7$ olefinic hydrocarbons is introduced into a depentanizer distillation tower and an overhead stream is separated comprising $C_5$- isoolefin-rich hydrocarbons and a bottom stream comprising $C_6$–$C_7$ olefinic hydrocarbons. The overhead stream and a light alkanol feedstream is introduced into an etherification zone in contact with acidic etherification catalyst under etherification conditions whereby alkyl tertiary alkyl ether is produced. The effluent from the etherification zone is separated in a distillation tower and a bottom stream is recovered comprising said alkyl tertiary alkyl ether and an overhead stream comprising unconverted $C_5$- hydrocarbons and unreacted alkanol. The depentanizer bottom stream and overhead stream from etherification is passed to an olefin interconversion zone in contact with acidic, medium pore metallosilicate particles under olefin interconversion conditions between 300° and 500° C. whereby an effluent stream rich in $C_5$- isoolefins is produced. The effluent stream is separated in a distillation tower and $C_4$–$C_5$ isoolefins are recovered for recycling to the etherification zone.

In a further embodiment of the invention the product from olefins interconversion is recycled to the depentanizer for separation.

DETAIL DESCRIPTION OF THE INVENTION

Figure 1:
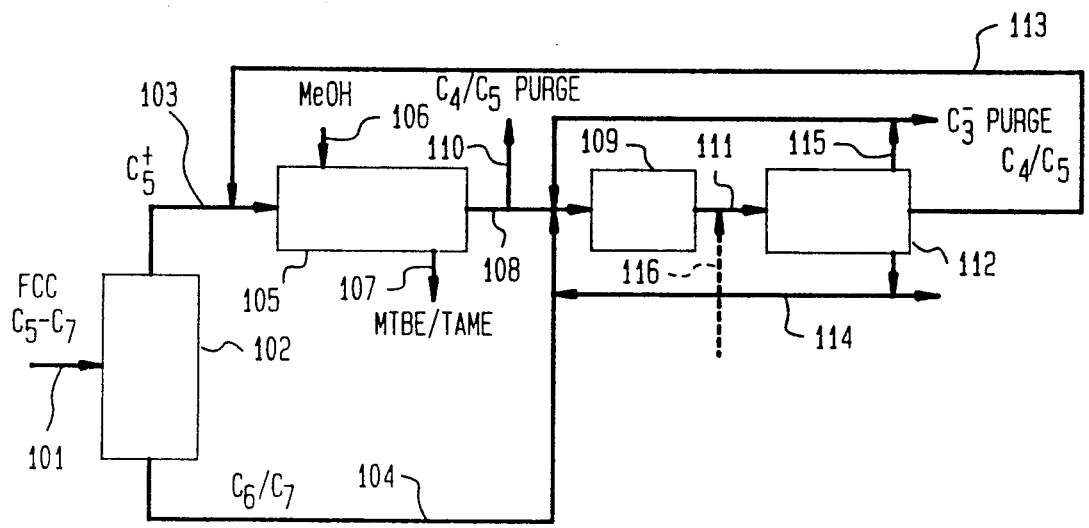
FIG. 1 is a schematic diagram illustrating a preferred process of the invention.

In the preferred embodiments of this invention methanol is reacted with a hydrocarbon feedstock containing olefins and particularly isoolefins such as isobutene and isoamylene to produce methyl tertiary butyl ethers, methyl tertiary amyl ether and other ethers.

Methanol ma be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites such as zeolite Beta and ZSM-5. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

In the process of this invention the term light alkanol includes methanol, ethanol, propanols and butanols, such as isopropanol and 1-butanol.

Processes for producing and recovering MTBE and other methyl tertiary alkyl ethers from $C_4$–$C_7$ isoolefins are known to those skilled in the art, such as disclosed in U.S. Pat. Nos. 4,544,776 (Osterburg, et al.) and 4,603,225 (Colaianne et al). Various suitable extraction and distillation techniques are known for recovering ether and hydrocarbon streams from etherification effluent.

In the process for catalytic conversion of oxygenate and/or olefins to heavier hydrocarbons by catalytic oligomerization using an acidic metallosilicate solid, including acid crystalline zeolite such as ZSM-5 type catalyst, process conditions can be varied to favor the formation of either gasoline, distillate, lube range products, aromatics or the interconversion of light olefins.

Typical reaction conditions for olefin interconversion as practiced in the instant invention comprise temperature between 650° F.–900° F. (343° C.–482° C.), preferably 750°–850° F. (399°–454° C.), at 0.5–20 weigh hourly space velocity (WHSV), pressure.

The olefin interconversion process requires the use of catalysts containing zeolites of controlled acidity (alpha value between 1 and 50, $SiO_2$ to $Al_2O_3$ ratio greater than 50), and with constraint index less than 12 to give high yields of the desired isoolefins while maintaining low selectivity to aromatics, paraffins, and cyclic compounds. Preferred catalysts include the highly siliceous zeolites of the MFI type as described in "Atlas of Zeolite Structure Types", by W. M. Meier and D. H. Olson, Butterworths, 1987. The method by which Constraint Index is determined is described fully in U.S. Pat. No. 4,016,218, to which reference is made for details of the method. Alpha value, or alpha number, is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980).

Preferred zeolites for the instant invention which have the specified values of Constraint Index and silica:alumina ratio include zeolites ZSM-5, ZSM-11, ZSM-12, ZSM-35, and ZSM-48, which are described in U.S. Pat. Nos. 3,702,886 (ZSM-5) and incorporated by reference, 3,709,979 (ZSM-11), 3,832,449 (ZSM-12), 4,076,842 (ZSM-23) and 4,016,245 (ZSM-35) and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5, but other cations e.g. rare earth cations may also be present. Metal cations such as Ga, Zn, Cu, Pt and Fe, can be introduced by conventional base exchange techniques. Catalysts containing phosphorous modified ZSM-5 can also be used. Conventional methods for preparing P-ZSM-5 catalysts have been disclosed in Butter et al U.S. Pat. Nos. 3,972,832 and 4,044,065.

TABLE 1

| OLEFIN INTERCONVERSION SINGLE PASS YIELDS | | |
|---|---|---|
| | $C_5$ Olefin Feed (Vol % of FF) | $C_6$ Olefin Feed (Vol % of FF) |
| $C_2$– | 0.83 | 0.88 |
| Propane | 2.56 | 2.71 |
| Propylene | 12.94 | 13.70 |
| 1-butane | 1.19 | 1.26 |
| N-butane | 0.67 | 0.71 |
| Butenes | 23.57 | 24.96 |
| 1-Pentane | 0.82 | 0.87 |
| N-pentane | 0.33 | 0.35 |
| 1-pentene | 14.62 | 15.48 |
| N-pentene | 5.11 | 5.41 |
| $C_5$+ saturates + cyclics | 6.85 | 7.25 |
| $C_6$+ linear olefins | 33.45 | 35.42 |
| TOTAL | 102.94 | 109.00 |

Typical yields produced employing the preferred catalyst and conditions described above for olefin interconversion of $C_5$ and $C_6$ olefins in a single pass process are shown in Table 1.

A preferred embodiment of the invention is illustrated in FIG. 1. Referring to FIG. 1, a light naphtha feedstream comprising $C_5-C_7$ olefinic hydrocarbons from a fluid catalytic cracking process is introduced 101 to depentanizer 102 and an overhead stream 103 comprising $C_5$-olefinic hydrocarbons and a bottom stream 104 comprising $C_6-C_7$ olefinic hydrocarbons are separated. The overhead stream 103 is passed to an etherification unit comprising an etherification reactor(s) containing acidic etherification catalyst and a distillation tower for separation of the etherification reaction product. An alkanol feedstream, typically methanol 106, is introduced to the etherification reactors under etherification conditions along with the overhead stream. The etherification reaction product is separated in the distillation tower and an etherification product 107 is recovered comprising methyl tertiary butyl ether and tertiary amyl methyl ether. Unreacted hydrocarbons and methanol are passed 108 to an olefins interconversion zone 109 containing ZSM-5 catalyst. A portion of the etherification reactor unconverted effluent is removed as purge stream 110 from which methanol is recovered by operations known in the art. The depentanizer bottom stream 104 is passed to the olefins interconversion unit concurrently with the etherification reactor unconverted product. In the olefins interconversion zone 109 olefin composition is converted to maximize the production of $C_4$ and $C_5$ isoolefins. The interconversion reactor effluent is passed 111 to fractionator 112 wherein $C_4-C_5$ isoolefins are separated and passed 113 as a feedstream to the etherification zone 105. $C_6+$ hydrocarbons separated from fractionator 112 can optionally be recycled 114 to the olefins interconversion unit 109. The $C_3$ fraction from fractionator 112 can optionally be separated and also recycled to the olefins interconversion unit. A portion of both the $C_6+$ stream and $C_3$ stream is removed as a purge stream.

Figure 2:
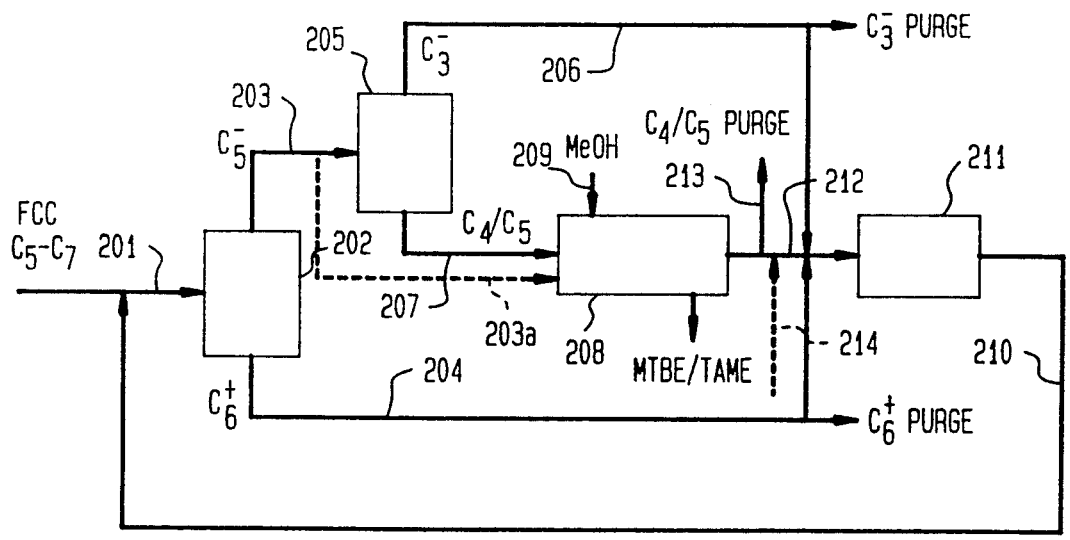
FIG. 2 is a schematic diagram showing a shared fractionation system for the invention.

Another preferred embodiment of the present invention is illustrated in FIG. 2. In this embodiment the effluent from the olefins etherification zone is separated by utilizing the depentanizer to separate both the feedstream and the effluent from olefins interconversion. Referring to FIG. 2, the $C_5-C_7$ feedstream is passed 201 to depentanizer 202 in conjunction with the effluent 210 from olefin interconversion unit 211. Overhead stream 203 is separated in depentanizer comprising $C_5$-olefinic hydrocarbons and a bottom stream 204 comprising $C_6-C_7$ hydrocarbons is recovered. The overhead stream 203 is passed to depropanizer 205 wherein an overhead stream 206 comprising $C_3$- hydrocarbons and a bottom stream 207 comprising $C_4-C_5$ isoolefins is separated. The bottom stream 207 is introduced to etherification zone 208 in conjunction with a methanol feedstream 209. The effluent from the etherification reaction zone is separated to recover MTBE and TAME and unreacted hydrocarbons and methanol are passed 212 to the olefins interconversion zone 211 in conjunction with the $C_3$- stream 206 and $C_6-C_7$ stream 204. A $C_4-C_5$ purge stream 213 is removed from the unconverted etherification effluent. Another embodiment of the invention depicted in FIG. 2 is shown in FIG. 2 by dash line 203a. Here the full stream 203 is passed directly to the etherification zone 208 eliminating vessel 205. For this embodiment stream 213 becomes a $C_5$- purge.

In both preferred embodiments, FIG. 1 and FIG. 2, supplemental light olefin feedstream can be introduced to the olefins interconversion zone via conduit 116 and 214 shown in dashed lines.

The di-olefins, sulfur, and nitrogen present in the FCC $C^5$ feed to the process of the invention require frequent catalyst regeneration. Accordingly, a fluid bed reactor configuration is preferred for olefin interconversion although fixed bed reactors can be utilized.

While the invention has been described by reference to specific embodiments, there is not intent to limit the scope of the invention except as described in the following claims.

What is claimed is:

1. A process for the production of high octane value alkyl tertiary alkyl ethers, comprising:
   (a) introducing a feedstream comprising $C_5-C_7$ olefinic hydrocarbons into a depentanizer distillation tower and separating an overhead stream comprising $C_5$- isoolefin-rich hydrocarbons and a bottom stream comprising $C_6-C_7$ olefinic hydrocarbons;
   (b) introducing said overhead stream and a light alkanol feedstream to an etherification zone in contact with acidic etherification catalyst under etherification conditions whereby alkyl tertiary alkyl ether is produced;
   (c) separating the effluent from said etherification zone in a distillation tower and recovering a bottom stream comprising said alkyl tertiary alkyl ether and an overhead stream comprising unconverted $C_5$- hydrocarbons and unreacted alkanol;
   (d) passing step (a) bottom stream and step (c) overhead stream to an olefin interconversion zone in contact with acidic, medium pore metallosilicate particles under olefin interconversion conditions between 300° and 500° C. whereby an effluent stream rich in $C_5$- isoolefins is produced;
   (e) separating step (d) effluent stream in a distillation tower and recovering $C_4-C_5$ isoolefins for recycling to step (b) etherification zone.

2. The process of claim 1 wherein said light alkanol is taken from the group consisting of methanol, ethanol, propanols and butanols.

3. The process of claim 1 wherein said alkanol comprises methanol whereby said alkyl tertiary alkyl ether comprises methyl tertiary butyl ether and methyl tertiary amyl ether.

4. The process of claim 1 wherein said metallosilicate comprises acidic zeolite.

5. The process of claim 4 wherein said zeolite has the structure of ZSM-5.

6. The process of claim 1 wherein said $C_5-C_7$ olefinic hydrocarbons comprises light naphtha from a fluid catalytic cracking process.

7. The process of claim 1 including the further step of introducing $C_4$- olefin supplemental hydrocarbon feedstream in step (d) interconversion zone.

8. A process for the production of alkyl tertiary butyl ether and alkyl tertiary amyl ether, comprising:
   (a) introducing a feedstream comprising $C_5-C_7$ olefinic hydrocarbons into a depentanizer distillation tower and separating an overhead stream comprising $C_5$- isoolefin-rich hydrocarbons and a bottom stream comprising $C_6-C_7$ olefinic hydrocarbons;
   (b) separating step (a) overhead stream in a depropanizer distillation tower to provide a depropanizer overhead stream comprising $C_3$- hydrocarbons and a depropanizer bottom stream comprising $C_4-C_5$ hydrocarbons rich in isoolefins;

(c) introducing step (b) bottom stream and a light alkanol feedstream to an etherification zone in contact with acidic etherification catalyst under etherification conditions whereby alkyl tertiary butyl ether and alkyl tertiary amyl ether are produced;

(d) separating the effluent from said etherification zone in a distillation tower and recovering a bottom stream comprising said ethers and an overhead stream comprising unconverted $C_4$–$C_5$ hydrocarbons and unreacted alkanol;

(e) passing step (a) bottom stream and step (b) and (d) overhead streams to an olefin interconversion zone in contact with acidic, medium pore metallosilicate particles under olefin interconversion conditions between 200° and 400° C. whereby an effluent stream rich in $C_5$- isoolefins is produced;

(f) passing step (e) effluent stream to step (a) distillation tower and recovering step (e) $C_5$- isoolefins as a portion of step (a) overhead.

9. The process of claim 8 wherein said light alkanol is taken from the group consisting of methanol, ethanol, propanols and butanols.

10. The process of claim 8 wherein said alkyl tertiary butyl ether and alkyl tertiary amyl ether comprise methyl tertiary butyl ether and methyl tertiary amyl ether.

11. The process of claim 8 wherein said metallosilicate comprises acidic zeolite.

12. The process of claim 11 wherein said zeolite has the structure of ZSM-5.

13. The process of claim 8 wherein said $C_5$–$C_7$ olefinic hydrocarbons comprises light naphtha from a fluid catalytic cracking process.

14. The process of claim 8 including the further step of introducing $C_4$- olefin supplemental hydrocarbon feedstream in step (e) interconversion zone.

15. The process of claim 1 including the step of purging a portion of step (d) overhead stream.

16. The process of claim 1 including the further step of recovering $C_3$- and $C_6+$ hydrocarbons streams in step (d) distillation and recycling said streams to step (d).

17. The process of claim 16 wherein an portion of said $C_3$- and $C_6+$ streams is purged.

18. The process of claim 8 including the step of purging a portion of step (b) overhead stream.

19. The process of claim 1 wherein the etherification catalyst comprises acid sulfonic acid resin solid.

20. The process of claim 8 including the further step of introducing a portion of step (a) overhead stream into step (c) etherification zone.

* * * * *